US010604558B2

(12) United States Patent
McNaughton et al.

(10) Patent No.: US 10,604,558 B2
(45) Date of Patent: Mar. 31, 2020

(54) COMPOSITIONS COMPRISING RESURFACED CELL-PENETRATING NANOBODIES AND METHODS OF USE THEREOF

(71) Applicant: Colorado State University Research Foundation, Fort Collins, CO (US)

(72) Inventors: Brian R. McNaughton, Fort Collins, CO (US); Virginia J. Bruce, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 236 days.

(21) Appl. No.: 15/398,368

(22) Filed: Jan. 4, 2017

(65) Prior Publication Data
US 2017/0204163 A1    Jul. 20, 2017

Related U.S. Application Data

(60) Provisional application No. 62/328,152, filed on Apr. 27, 2016, provisional application No. 62/274,886, filed on Jan. 5, 2016.

(51) Int. Cl.
| | |
|---|---|
| *C07K 16/00* | (2006.01) |
| *G01N 33/531* | (2006.01) |
| *G01N 33/532* | (2006.01) |
| *G01N 33/533* | (2006.01) |
| *C07K 16/40* | (2006.01) |
| *C07K 16/32* | (2006.01) |
| *G01N 33/53* | (2006.01) |

(52) U.S. Cl.
CPC .............. *C07K 16/00* (2013.01); *C07K 16/32* (2013.01); *C07K 16/40* (2013.01); *G01N 33/53* (2013.01); *G01N 33/531* (2013.01); *G01N 33/532* (2013.01); *G01N 33/533* (2013.01); *C07K 2317/567* (2013.01); *C07K 2317/569* (2013.01); *C07K 2317/77* (2013.01)

(58) Field of Classification Search
CPC ........ C07K 16/00; C07K 16/32; C07K 16/40; G01N 33/53; G01N 33/531; G01N 33/532; G01N 33/533
See application file for complete search history.

(56) References Cited

U.S. PATENT DOCUMENTS

| | | | |
|---|---|---|---|
| 8,623,349 B2 * | 1/2014 | Fernandez Herrero | ...................... C07K 16/00 424/1.49 |
| 8,975,382 B2 * | 3/2015 | Revets | ............... C07K 16/2863 530/388.8 |
| 2011/0112040 A1 | 5/2011 | Liu et al. | |
| 2014/0186265 A1 | 7/2014 | McNaughton et al. | |
| 2015/0266939 A1 * | 9/2015 | Vogan | .................... C07K 14/50 424/135.1 |

OTHER PUBLICATIONS

Li et al. Cell-penetrating anti-GFAP VHH and corresponding fluorescent fusion protein VHH-GFP spontaneously cross the blood-brain barrier and specifically recognize astrocytes: application to brain imaging. Faseb J. 26: 3969-3979 (2012).*
Kubala et al. Structural and Thermodynamic analysis of the GFP:GFP-nanobody complex. Protein Science 19:2389-2401 (2010).*
Bruce et al. Resurfaced Cell-Penetrating Nanobodies: A Potentially General Scaffold for Intracellularly Targeted Protein Discovery. Protein Science, Jun. 1, 2016, vol. 25, pp. 1129-1137.
International Search Report and Written Opinion, PCT/US2017/012160, dated May 5, 2017.
Kubala et al. Structural and Thermodynamic Analysis of the GFP:GFP-Nanobody Complex. Protein Science, Dec. 1, 2010, vol. 19, pp. 2389-2401.
Lawrence et al. Supercharging Proteins can Impart Unusual Resilience. Journal of the American Chemical Society, Aug. 22, 2007, vol. 129, pp. 10110-10112.
Thompson et al. Engineering and Identifying Supercharged Proteins for Macromolecule Delivery into Mammalian Cells. Methods in Enzymology, Nov. 23, 2012, vol. 503, pp. 293-319.

* cited by examiner

Primary Examiner — Gailene Gabel
(74) Attorney, Agent, or Firm — Polsinelli PC

(57) ABSTRACT

The disclosure encompasses resurfaced cell-penetrating nanobodies and their methods of use. The resurfacing of nanobodies with positively-charged amino acids facilitates their penetration into a cell and allows targeting of a specific intracellular protein.

17 Claims, 8 Drawing Sheets

Specification includes a Sequence Listing.

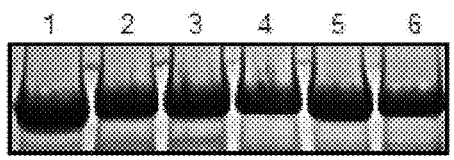
FIG. 2A
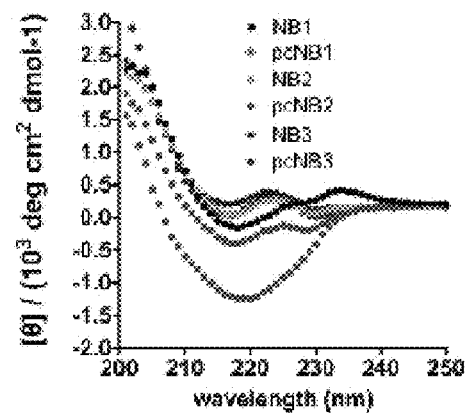
FIG. 2B
FIG. 2C

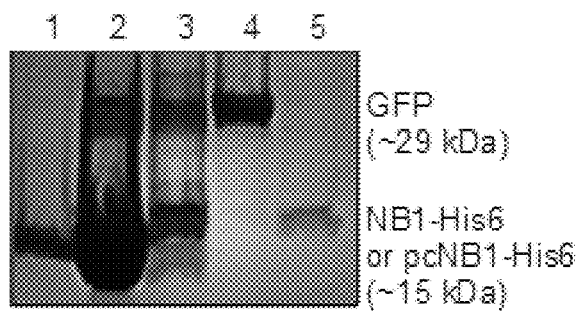 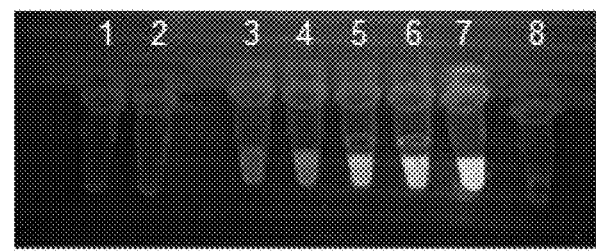
FIG. 4A                                       FIG. 4B

COMPOSITIONS COMPRISING RESURFACED CELL-PENETRATING NANOBODIES AND METHODS OF USE THEREOF

CROSS REFERENCE TO RELATED APPLICATION

The present application claims priority to U.S. Provisional Patent Application No. 62/328,152 filed Apr. 27, 2016 and U.S. Provisional Patent Application No. 62/274,886 filed Jan. 5, 2016. The contents of the above-mentioned patent applications are hereby incorporated by reference in their entirety.

REFERENCE TO SEQUENCE LISTING

A paper copy of the sequence listing and a computer readable form of the same sequence listing are appended below and herein incorporated by reference. The information recorded in the computer readable form is identical to the written sequence listing, according to 37 C.F.R. § 1.821(f).

FIELD OF THE INVENTION

The disclosure encompasses resurfaced cell-penetrating nanobodies and their methods of use. The resurfacing of nanobodies with positively-charged amino acids facilitates their penetration into a cell and allows targeting of a specific intracellular protein.

BACKGROUND OF THE INVENTION

By virtue of their size, functional group diversity, and complex structure, proteins can often recognize and modulate disease-relevant macromolecules that present a challenge to small-molecule reagents. Additionally, high-throughput screening and evolution-based methods often make the discovery of new protein binders simpler than the analogous small-molecule focused process. However, most proteins do not cross the lipid bilayer membrane of mammalian cells. This largely limits the scope of protein therapeutics and basic research tools to those targeting disease-relevant receptors on the cell surface or extracellular matrix. Previously, researchers have shown that cationic resurfacing of proteins can endow cell penetration. However, many proteins are not amenable to such extensive mutagenesis. Relatively little is known about how to dramatically resurface a protein with a polycationic feature in a manner that does not dramatically alter or abolish its utility and/or function (stability, target affinity, expression in E. coli). Even structurally similar proteins respond differently to such extensive mutagenesis, and many proteins of therapeutic interest were not amenable to polycationic resurfacing.

Thus, there is a need in the art for the development of a protein scaffold that is amenable to cationic resurfacing and can penetrate the cell while also being able to recognize a magnitude of intracellular targets. Such a protein would represent a general scaffold for intracellular targeted protein therapeutic discovery.

BRIEF SUMMARY OF THE INVENTION

The present disclosure provides a nanobody that is able to penetrate the lipid bilayer membrane of a cell. The cell-penetrating nanobody comprises a modified framework region having an exposed polycationic surface. The modified framework region may be a variant of a wild-type nanobody in which one or more amino acid residues are substituted with arginine or lysine. The modified framework region of the cell-penetrating nanobody may have a theoretical net charge ranging from about +10 to about +35. Alternatively, the cell-penetrating protein may have a theoretical net charge ranging from about +10 to about +25. The cell-penetrating nanobody may be fused to a reporter protein. The reporter protein may be chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune). The framework region of the cell-penetrating nanobody may comprise the framework protein sequence selected from the group consisting of pcNB1, pcNB2, and pcNB3.

In another aspect, the present disclosure provides a method of binding a target protein. The method may include providing a cell-penetrating nanobody, having binding affinity for the target protein and comprising a modified framework region having an exposed polycationic surface; and contacting the target protein with the cell-penetrating nanobody in the cytosol of a cell. The modified framework region of the cell-penetrating antibody may be a variant of a wild-type nanobody in which one or more amino acid residues are substituted with arginine or lysine. The cell-penetrating nanobody may have a theoretical net charge ranging from about +10 to about +35. Alternatively, the cell-penetrating protein may have a theoretical net charge ranging from about +10 to about +25. The cell-penetrating nanobody may further be fused to a reporter protein. The reporter protein may be chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune). The framework region of the cell-penetrating nanobody may comprise the framework protein sequence selected from the group consisting of pcNB1, pcNB2, and pcNB3.

In an additional aspect, the present disclosure provides a method of detecting a target protein. The method may include providing a cell-penetrating nanobody; and contacting the target protein with the cell-penetrating nanobody in the cytosol of a cell. The cell-penetrating nanobody may comprise a modified framework region having an exposed polycationic surface. The modified framework region may be a variant of a wild-type nanobody in which one or more amino acid residues are substituted with arginine or lysine. The cell-penetrating nanobody having a theoretical net charge ranging from about +10 to about +35. Alternatively, the cell-penetrating protein may have a theoretical net charge ranging from about +10 to about +25. The cell-penetrating nanobody may have binding affinity for the target protein. The cell-penetrating nanobody may be fused to a reporter protein. The reporter protein may be chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune). The framework region of the cell-penetrating nanobody may comprise the framework protein sequence selected from the group consisting of pcNB1, pcNB2, and pcNB3.

In a further aspect, the present disclosure provides a method of preparing a cell-penetrating protein. The method may include modifying a wild-type nanobody by mutating at least one amino acid residue in the framework region to arginine or lysine. The cell-penetrating protein may have a theoretical net charge ranging from about +10 to about +35. Alternatively, the cell-penetrating protein may have a theoretical net charge ranging from about +10 to about +25. The cell-penetrating nanobody may be fused to a reporter protein. The reporter protein is chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune). The framework region of the cell-penetrating nanobody may comprise the framework protein sequence selected from the group consisting of pcNB1, pcNB2, and pcNB3.

BRIEF DESCRIPTION OF THE FIGURES

FIG. 2A depicts the sequence of wild-type nanobodies: NB1 (SEQ ID NO:1—MGMQVQLVESGGALVQPGGSL-RLSCAASGFPVNRYSMRWYRQAPGKEREWVAGM SSAGDRSSYEDSVKGRFTISRDDARNTVYLQMNSLK-PEDTAVYYCNVNVGFEYWGQ GTQVTVSSHHH-HHH), NB2 (SEQ ID NO:2—MEVQLVESGGGLVQAGG-SLRLSCAASGITFSINTMGWYRQAPGKQRELVALISS IGDT YYADSVKGRFTISRDNAKNTVYLQMNSLK-PEDTAVYYCKRFRTAAQGTDYWGQGTQV TVSSHH-HHHH), and NB3 (SEQ ID NO:3—MAQVQLVESGGGS-VQAGGSLRLSCTASGGSEYSYSTFSLGWFRQAPGQE REAVAA1 ASMGGLTYYADSVKGRFTISRDNAKNT-VTLQMNNLKPEDTAIYYCAAVRGYFMRLPSS HNFRYWGQGTQVTVSSHHHHHH) and resurfaced polycationic nanobodies: pcNB1 (SEQ ID NO:4—MQVQLVEKGGKRVQPGGSLRLKCAASGFPVN-RYSMRWYRQAPGKEREWVAGMSS AGDRSSYEDSVKGRFKIKRDDARNTVYLRMRKLK-PEDTAVYYCNVNVGFEYWGQGT RVTVSKKHHH-HHH), pcNB2 (SEQ ID NO:5—MEVQLVEK-GGGRVQAGGSLRLRCAASGITFSINTMGWYRQAPG KQRELVALISSIGDT YYADSVKGRFRIRRDNAKNT-VYLRMRRLKPEDTAVYYCKRFRTAAQGTDY-WGQGTR VTVSKHHHHHH), and pcNB3 (SEQ ID NO:6—MAQVQLVEKGGGKVRAGGKLRL-RCTASGGSEYSYSTFSLGWFRQAPGQEREAVAAI ASMGGLTYYADSVKGRFKIKRDNAKNTVTLRMNN-LKPEDTAIYYCAAVRGYFMRLPSS HNFRYWGQG-TRVTVSRHHHHHH). FIG. 2B depicts a PAGE analysis of wild-type (NB1-3) and resurfaced polycationic (pcNB1-3) nanobodies. FIG. 2C depicts a circular dichroism spectra of wild-type (NB1-3) and resurfaced polycationic (pcNB1-3) nanobodies.

FIG. 4A depicts a Coommassie stain of purified protein from co-expression of $His_6$-labeled NB1 or pcNB1 and untagged GFP in E. coli from a pET-DUET plasmid. Lane 1: $His_6$-NB1; Lane 2: co-purification of untagged GFP with $His_6$-NB1 from E. coli cell lysate; Lane 3: co-purification of untagged GFP with $His_6$-pcNB1; Lane 4: $His_6$-GFP; Lane 5: $His_6$-pcNB1. FIG. 4B depicts images analyzing by a long wave (365 nm) hand-held lamp for the presence of GFP. $His_6$-NB1 and $His_6$-pcNB1 recovered from thermal denaturation and regained function (GFP affinity). Tube 1: $His_6$-NB1; Tube 2: $His_6$-pcNB1; Tubes 3-4: $His_6$-NB1 and co-eluted GFP; Tubes 5-6: $His_6$-pcNB1 and co-eluted GFP; Tube 7: $His_6$-GFP; Tube 8: untagged GFP.

FIG. 6A depicts treatment with pcNB1. FIG. 6B depicts treatment with pcNB2. FIG. 6C depicts treatment with pcNB3.

DETAILED DESCRIPTION OF THE INVENTION

Figure 1A:
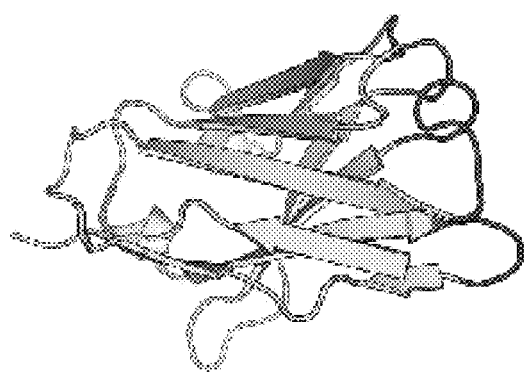
FIG. 1A depicts a nanobody that binds Green Fluorescent Protein (GFP) (NB1). Complementarity-determining region (CDR) loops are highlighted in purple.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including," as well as other forms, such as "includes" and "included," is not limiting.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. Enzymatic and staining reactions, and purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also those well known and commonly used in the art.

Described herein are nanobodies—a small and stable protein that can be evolved to recognize virtually any disease-relevant receptor—that are amenable to cationic resurfacing, resulting in potent cell penetration. As described herein, polycationic resurfacing does not appreciably alter the structure, expression, and function (target recognition) of the nanobody. Further, it is demonstrated that multiple nanobodies are amenable to polycationic resurfacing, and that the majority of cell-penetrating nanobodies access the cytosol. Accordingly, resurfaced polycationic cell-penetrating nanobodies represent a general scaffold for intracellular targeted protein therapeutic discovery. Various aspects of the cell-penetrating nanobodies and methods of use thereof are described in detail below.

As will be realized, the disclosed aspects are capable of modifications in various aspects, all without departing from the spirit and scope of the present disclosure. Accordingly, all sections of the present disclosure, including the Summary, Drawings, and Detailed Description are to be regarded as illustrative in nature and not restrictive.

I. Cell-Penetrating Nanobody

In an aspect, the present disclosure provides a cell-penetrating nanobody comprising a modified framework region having an exposed polycationic surface. As used herein, a "nanobody" refers to a single-domain antibody, generally designated sdAb, which is an antibody fragment consisting of a single monomeric variable antibody domain which is able to bind selectively to an antigen. A nanobody may comprise heavy chain variable domains or light chain variable domains. Specifically, a nanobody of the disclosure comprises heavy chain variable domain. A nanobody may be derived from camelids ($V_HH$ fragments) or cartilaginous fishes ($V_{NAR}$ fragments). Alternatively, a nanobody may be derived from splitting the dimeric variable domains from IgG into monomers.

A nanobody comprises a variable region primarily responsible for antigen recognition and binding and a framework region. The "variable region," also called the "complementarity determining region" (CDR), comprises loops which differ extensively in size and sequence based on antigen recognition. CDRs are generally responsible for the binding specificity of the nanobody. Distinct from the CDRs is the framework region. The framework region is relatively conserved and assists in overall protein structure. The framework region may comprise a large solvent-exposed surface consisting of a β-sheet and loop structure.

The framework region of a nanobody of this disclosure is modified to have an exposed polycationic surface. It is to be understood that modification of the nanobody to comprise an exposed polycationic surface does not appreciably alter the structure, expression, and function (antigen recognition) of the nanobody. Without wishing to be bound by theory, polycationic modification of the surface of the nanobody enhances cell-penetration of the nanobody thereby allowing intracellular antigens to be targeted. For example, the framework region of a wild-type nanobody may be modified to comprise one or more positively charged amino acid residues.

As used herein, a "polycationic surface" is a surface of a nanobody comprising one or more positively charged amino acid residues.

As used herein, a "wild-type nanobody," also referred to as a "naturally occurring nanobody" is a nanobody naturally found in nature after exposure to an antigen, including allelic variances. Additionally, a "wild-type nanobody" is any nanobody sequence prior to modification to comprise an exposed polycationic surface.

A positively charged amino acid residue may be a naturally occurring amino acid, a synthetic amino acid, a genetically encoded amino acid, a non-genetically encoded amino acid, and a combination thereof, provided it is positively-charged. Non-limiting examples of positively-charged amino acid residues include lysine (K), arginine (R), and to a limited extent histidine (H) at pH values of less than about 6.

The incorporation of a polycationic surface onto a nanobody increases the theoretical net charge of the nanobody. For example, a neutral nanobody with a relatively small net theoretical charge, defined herein as a theoretical charge magnitude of less than about 5, is mutagenized by substituting one or more positively-charged amino acids into the amino acid sequence of the neutral nanobody. In an aspect, a positively-charged amino acid may be substituted for a neutral or negatively-charged amino acid to increase the net positive theoretical charge of a nanobody. The substitution of a positively-charged amino acid for a negatively-charged amino acid results in a larger change in net theoretical charge magnitude than a substitution for a neutral amino acid.

In an aspect, the cell-penetrating nanobody may have a net positive theoretical charge ranging from about +5 to about +50. For example, a theoretical net charge may range from about +5 to about +35, about +10 to about +35, about +10 to about +30, about +10 to about +25, or about +10 to about +20. Specifically, a theoretical net charge may be about +14 or about +15. The magnitude of the net theoretical charge may influence one or more characteristics of the nanobody including, but not limited to the protein's susceptibility to aggregation within a cell, the solubility of the protein, the stability of the protein, and any combination thereof. In one additional aspect, the magnitude of positive net theoretical charge may further influence the ability of the nanobody to penetrate a target cell.

Any number of amino acid substitutions in the framework region may be performed to obtain a polycationic surface onto a nanobody, so long as the nanobody is still able to penetrate a target cell. In an aspect, a framework region of a nanobody may be modified to comprise one or more amino acid residues selected from the group consisting of lysine and arginine. In a further aspect, the solvent exposed residues of the framework region of a nanobody may be modified to comprise one or more positively-charged amino acids residues. More specifically, the large solvent-exposed surface consisting of a β-sheet and loop structure of the framework region of a nanobody may be modified to comprise one or more positively-charged amino acid residues. For example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more residues of the framework region may be mutated to positively-charged amino acid residues. Accordingly, a framework region of a nanobody may be modified to comprise 1, 2, 3, 4, 5, 6, 7, 8, 9, 10, 11, 12, 13, 14, 15, 16, 17, 18, 19, or 20 or more positively-charged amino acid residues. Specifically, a framework region of a nanobody may be modified to comprise at least nine positively-charged amino acid residues. In other embodiments, a framework region of a nanobody may be modified to comprise eleven positively-charge amino acid residues.

In another aspect, the modified framework region of the nanobody comprises the framework protein sequence selected from the group consisting of pcNB1, pcNB2, and pcNB3. In another aspect, the modified framework region of the nanobody consists of the framework protein sequence selected from the group consisting of pcNB1, pcNB2, and pcNB3. The framework protein sequence pcNB1 is SEQ ID NO: 7—CDR1-SEQ ID NO:8-CDR2-SEQ ID NO:9—CDR3-SEQ ID NO:10 (i.e., MQVQLVEKGGKRVQPGG-SLRLKCAAS-CDR1-MRWYRQAPGKEREWVAG-CDR2-YEDSVKGRFKIKRDDARNTVYLRMRKLKPEDTAVYYC-CDR3-YWGQGTRVTVSKK); the framework protein sequence pcNB2 is SEQ ID: 11—CDR1-SEQ ID NO:12—CDR2-SEQ ID NO:13—CDR3-SEQ ID NO:14 (i.e. MEVQLVEKGGGRVQAGGSLRLRCAAS-CDR1-WYRQAPGKQRELVAL-CDR2-ADSVKGRFRIRRD-NAKNTVYLRMRRLKPEDTAVYYC-CDR3-YWGQG-TRVTVSK); the framework protein sequence pcNB3 is SEQ ID:15—CDR1-SEQ ID NO:16—CDR2-SEQ ID NO:17—CDR3-SEQ ID NO:18 (i.e., SEQ ID NO:9—MAQVQLVEKGGGKVRAGGKLRLRCTAS-CDR1-WFRQAPGQEREAVA-CDR2-RFKIKRDNAKNTVTL-RMNNLKPEDTAIYYCAA-CDR3-WGQGTRVTVSR); wherein CDR1, CDR2 and CDR3 are modified based on the target protein. In still another aspect, the modified framework region of the nanobody is a sequence comprising at least 80% identity to SEQ ID NO:7, SEQ ID NO:8, SEQ ID NO:9 and SEQ ID NO:10. In still another aspect, the modified framework region of the nanobody is a sequence comprising at least 80% identity to SEQ ID NO:11, SEQ ID NO:12, SEQ ID NO:13, and SEQ ID NO:14. In still another aspect, the modified framework region of the nanobody is a sequence comprising at least 80% identity to SEQ ID NO:15, SEQ ID NO:16, SEQ ID NO:17 and SEQ ID NO:18. For example, the modified framework region of the nanobody may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:7, 8, 9 and 10, or SEQ ID NO: 11, 12, 13 and 14, or SEQ ID NO: 15, 16, 17, and 18, provided the modified framework region maintains the polycationic surface.

A nanobody may further comprise a reporter protein or therapeutic agent. The reporter protein or therapeutic agent may be fused directly to the nanobody or indirectly to the nanobody via a linker. It is to be understood that conjugation of the nanobody to the reporter protein or therapeutic or conjugation of the nanobody to the linker and conjugation of the linker to the reporter protein or therapeutic agent will not adversely affect either the targeting function of the nanobody or the reporter function of the protein or the therapeutic action of the therapeutic agent. Suitable linkers include amino acid chains and alkyl chains functionalized with reactive groups for coupling to both the nanobody and the reporter protein. An amino acid chain linker may be about 1 to about 40 residues, more often about 1 to about 10 residues. Typical amino acids residues used for linking are tyrosine, cysteine, lysine, glutamic and aspartic acid, and the like. In some instances, a nanobody may be generated with a cleavable linker between the nanobody and the reporter protein or therapeutic agent. A "cleavable linker" as used herein is an amino acid linker that comprises a site susceptible to cleavage by an enzyme. Such a linker may allow release of the reporter protein or therapeutic agent at a specific cellular location. The enzyme may be an enzyme that is associated with a disease or condition. Non-limiting examples of a disease or condition include cancer, cardiovascular disease, arthritis, viral, bacterial, parasitic or fungal infection, Alzheimer's disease, emphysema, thrombosis, hemophilia, stroke, organ dysfunction, any inflammatory condition, vascular disease, parenchymal disease, or a pharmacologically-induced state. Non-limiting examples of sites susceptible to cleavage include a MMP sensitive site, a caspase-sensitive site, a kallikrein sensitive site, a cathepsin sensitive site, a plasminogen activator sensitive site and/or an ADAM sensitive site.

A "therapeutic agent" is any compound known in the art that is used in the detection, diagnosis, or treatment of a condition or disease. Such compounds may be naturally-occurring, modified, or synthetic. Non-limiting examples of therapeutic agents may include drugs, therapeutic compounds, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Non-limiting examples of therapeutic agents may include immune-related agents, thyroid agents, respiratory products, antineoplastic agents, antihelmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, antivirals, anti-anginals, antibiotics, anti-inflammatories, anti-rheumatics, narcotics, cardiac glycosides, neuromuscular blockers, sedatives, local anesthetics, general anesthetics, or radioactive atoms or ions. A therapeutic agent may be a toxin, a small molecule therapeutic, a therapeutic nucleic acid, or a chemotherapeutic agent. A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells.

"Reporter protein," as used herein, refers to any protein capable of generating a detectable signal within a cell. Reporter proteins typically fluoresce, catalyze a colorimetric or fluorescent reaction, or endow a host cell with resistance to an exogenous toxin. Non-limiting examples of a reporter protein includes a fluorescent protein, luciferase, alkaline phosphatase, β-galactosidase, β-lactamase, dihydrofolate reductase, ubiquitin, horseradish peroxidase, and variants thereof. Non-limiting examples of reporter proteins that fluoresce include green fluorescent proteins (GFP), red fluorescent proteins (YFP), yellow fluorescent proteins (YFP), blue fluorescent proteins such as TagBFP (Evrogen), cyan fluorescent proteins, yellow fluorescent proteins, orange fluorescent proteins, and far-red fluorescent proteins such as mNeptune. Non-limiting examples of green fluorescent proteins include: mTagBFP2 (Evrogen), EGFP, Emerald, Superfolder GFP, Monomeric Azami Green (MBL International), TagGFP2 (Evrogen), mUKG, mWasabi (Allele Biotech), Clover, and mNeonGreen (Allele Biotech). Non-limiting examples of red fluorescent proteins include: mRaspberry, mCherry, mStrawberry, mTangerine, tdTomato, Tag RFP (Evrogen), Tag RFP-T, maple, mRuby, and mRuby2. Non-limiting examples of cyan fluorescent proteins include: monomeric Midoriishi-Cyan (MBL International); Tag CFP (Evrogen); and mTFP1 (Allele Biotech). Non-limiting examples of yellow fluorescent proteins include: EYFP, Citrine, Venus, SYFP2, and TagYFP (Evrogen). The sequences of fluorescent proteins, their characteristics (e.g., excitation and emission wavelengths, extinction coefficients, brightness and pKa) are generally detailed in the source literature well known to those of routine skill in the art.

Non-limiting examples of reporter proteins that catalyze a colorimetric or fluorescent reaction include luciferase. Non-limiting examples of proteins that endow a host cell with resistance to an exogenous toxin include dihydrofolate reductase (DHFR), β-lactamase, and β-galactosidase.

In one aspect, the reporter protein is a superpositive reporter protein. "Superpositive reporter protein," as referred to herein, refers to any highly mutagenized variant of a neutral reporter protein with a relatively high theoretical positive charge that is resistant to aggregation, among other advantageous properties. In one aspect, a neutral reporter protein with a relatively small net theoretical charge, defined herein as a theoretical charge magnitude of less than about 5, is mutagenized by substituting one or more positively-charged amino acids into the amino acid sequence of the neutral reporter protein. In an aspect, a positively-charged amino acid may be substituted for a neutral or negatively-charged amino acid to increase the net positive theoretical charge of a reporter protein. The substitution of a positively-charged amino acid for a negatively-charged amino acid, results in a larger change in net theoretical charge magnitude than a substitution for a neutral amino acid. In an aspect, the superpositive reporter protein may have a net positive theoretical charge ranging from about +5 to about +50. The magnitude of the net theoretical charge may influence one or more characteristics of the superpositive reporter protein including, but not limited to the protein's susceptibility to aggregation within a cell, the solubility of the protein, the stability of the protein, and any combination thereof. In one additional aspect, the magnitude of positive net theoretical charge may further influence the ability of the superpositive reporter protein to penetrate a target cell. Specifically, the reporter protein is chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune).

A nanobody is capable of specifically binding to a target protein. A target protein may include any protein, protein fragment, peptide, or amino acid. The phrase "specifically binds" herein means nanobodies bind to a target protein with an affinity constant or Affinity of interaction ($K_D$) in the range of at least 0.1 mM to 1 pM, or in the range of at least 0.1 pM to 100 nM, with a preferred range being 1 nM to 100 nM.

The nanobody may naturally specifically bind a target protein or the nanobody may be modified to specifically bind a target protein. A nanobody that naturally specifically binds a target protein may be obtained by immunizing a subject capable of producing a nanobody with a target protein and isolating a nanobody from the serum of the subject. Alternatively, CDRs known to specifically bind a target protein may be grafted onto a nanobody framework region. The assignment of amino acid sequences to each CDR may be in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883). Further, high-throughput screening may be used to identify a nanobody that specifically binds to a target protein. Still further, in vitro evolution methods may be used to generate a nanobody that specifically binds a target protein. The phrase "in vitro evolution" generally means any method of selecting for a nanobody that binds to a target protein. In vitro evolution is also known as "in vitro selection", "SELEX," or "systematic evolution of ligands by exponential enrichment." Briefly, in vitro evolution involves screening a pool of random nanobodies for a particular nanobody that binds to a target protein or has a particular activity that is selectable. Accordingly, in vitro evolution is used to generate nanobodies that specifically bind to distinct epitopes of any given target protein.

The target protein may be intracellular or extracellular to a target cell. The target protein may be on the surface of a target cell or inside a target cell. Specifically, a target protein may be an intracellular receptor within a target cell. Accordingly, a nanobody comprising a polycationic surface is capable of specifically binding to an intracellular target protein. Importantly, a single nanobody comprising a polycationic surface may be used to produce several different nanobodies that are each capable of specifically binding to a different intracellular target protein. In such a scenario, the framework region comprising the polycationic surface is kept constant while the CDR region or variable region is modified to specifically bind to a desired intracellular target in a target cell.

A target cell may be any mammalian cell including, but not limited to a cancer cell, an immune system cell, and any other mammalian cell of interest. The cancer cell may be disposed in a subject.

The cancer cell may be a blood cancer cell (e.g., leukemia, lymphoma, myeloma) or a solid tumor cancer cell. Non-limiting examples of cancer cells include bladder cancer cells, bone cancer cells, brain cancer cells, breast cancer cells, central nervous system cancer cells, cervical cancer cells, colon cancer cells, colorectal cancer cells, duodenal cancer cells, endometrial cancer cells, esophageal cancer cells, eye cancer cells, gallbladder cancer cells, germ cell cancer cells, kidney cancer cells, larynx cancer cells, leukemia cells, liver cancer cells, lymphoma cells, lung cancer cells, melanoma cells, mouth/throat cancer cells, ovarian cancer cells, pancreatic cancer cells, prostate cancer cells, skin cancer cells, testicular cancer cells, thyroid cancer cells, vaginal cancer cells, and drug resistant cancer cells. Non-limiting examples of immune system cells include: phagocytes such as macrophages, neutrophils, and dendritic cells; mast cells; eosinophils; basophils; natural killer cells; B cells; and T cells such as killer T cells, helper T cells, and γδ T cells. The immune cells may further include immune cells at a particular activation state in various aspects.

(a) Nanobody Construct

In an aspect, the present disclosure provides a nanobody construct. A nanobody construct of the disclosure is a polynucleotide sequence encoding a polypeptide, the polypeptide comprising a cell-penetrating nanobody. Further, a nanobody construct of the disclosure is a polynucleotide sequence encoding a polypeptide, the polypeptide comprising a cell-penetrating nanobody fused to a reporter protein or therapeutic agent. As used herein, the terms "polynucleotide sequence of the disclosure" and "nanobody construct" are interchangeable. The present disclosure also provides isolated polypeptides encoded by nanobody constructs, vectors comprising nanobody constructs, and isolated cells comprising said vectors.

i. Polynucleotide Sequence

A nanobody construct of the disclosure is a polynucleotide sequence encoding a polypeptide, the polypeptide comprising a cell-penetrating nanobody. The polypeptide comprising the cell-penetrating nanobody may further comprise a reporter protein or a therapeutic agent. Additionally, the polynucleotide sequence of the disclosure may encode a polypeptide comprising the cell-penetrating nanobody that further comprises a linker linking the nanobody to the reporter protein or therapeutic agent. The cell-penetrating nanobody is capable of penetrating a target cell and specifically binding to an intracellular target protein.

Each of the above embodiments may optionally comprise a signal peptide and/or a purification moiety. When present, typically the polynucleotide sequence encoding the signal peptide is at the N-terminus of the nanobody construct and the polynucleotide sequence encoding the purification moiety is at the C-terminus of the nanobody construct. Alternatively, the polynucleotide sequence encoding the signal peptide and the polynucleotide sequence encoding the purification moiety are both at the N-terminus of the nanobody construct. The choice of polynucleotide sequence encoding the signal peptide can and will vary depending on a variety factors including, but not limited to, the desired cellular location and type of cell. Suitable polynucleotide sequence encoding signal peptides are known in the art, as are polypeptide sequences encoded therefrom. Similarly, the choice of purification moiety can and will vary. Suitable purification moieties are known in the art, as are the polynucleotide sequences encoding them. In a specific embodiment, the purification moiety is a histidine tag.

In each of the above embodiments, a "nanobody," a "reporter protein," a "therapeutic agent," and a "linker" may be as described in detail above in Section I, which is hereby incorporated by reference into this section.

Polynucleotide sequences of the disclosure may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the disclosure. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

ii. Polypeptide Sequence

In another aspect, the present disclosure provides one or more isolated polypeptide(s) encoded by a polynucleotide sequence of the disclosure. Polynucleotide sequences of the disclosure are described in detail in Section I(a)i, and are hereby incorporated by reference into this section. An isolated polypeptide of the disclosure comprises a cell-penetrating nanobody. The polypeptide comprising the cell-penetrating nanobody may further comprise a reporter protein or a therapeutic agent. Additionally, the polypeptide comprising the cell-penetrating nanobody may further comprise a linker linking the nanobody to the reporter protein or therapeutic agent. The cell-penetrating nanobody is capable of penetrating a target cell and specifically binding to an intracellular target protein.

In an aspect, a polypeptide sequence comprises SEQ ID NO: 7—CDR1-SEQ ID NO:8—CDR2-SEQ ID NO:9—CDR3-SEQ ID NO:10 (i.e., MQVQLVEKGGKRVQPGGSLRLKCAAS-CDR1-MRWYRQAPGKEREWVAG-CDR2-YEDSVKGRFKIKRDDARNTVYLRMRKLKPEDTAVYYC-CDR3-YWGQGTRVTVSKK); the framework protein sequence pcNB2 is SEQ ID: 11—CDR1-SEQ ID NO:12—CDR2-SEQ ID NO:13—CDR3-SEQ ID NO:14 (i.e. MEVQLVEKGGGRVQAGGSLRLRCAAS-CDR1-WYRQAPGKQRELVAL-CDR2-ADSVKGRFRIRRD-NAKNTVYLRMRRLKPEDTAVYYC-CDR3-YWGQGTRVTVSK); the framework protein sequence pcNB3 is SEQ ID:15—CDR1-SEQ ID NO:16—CDR2-SEQ ID NO:17—CDR3-SEQ ID NO:18 (i.e., SEQ ID NO:9—MAQVQLVEKGGGKVRAGGKLRLRCTAS-CDR1-WFRQAPGQEREAVA-CDR2-RFKIKRDNAKNTVTL-RMNNLKPEDTAIYYCAA-CDR3-WGQGTRVTVSR); wherein CDR1, CDR2 and CDR3 are modified based on the target protein. In another aspect, the polypeptide sequence consists of SEQ ID NO: 7—CDR1-SEQ ID NO:8—CDR2-SEQ ID NO:9—CDR3-SEQ ID NO:10 (i.e., MQVQLVEKGGKRVQPGGSLRLKCAAS-CDR1-MRWYRQAPGKEREWVAG-CDR2-YEDSVKGRFKIKRDDARNTVYLRMRKLKPEDTAVYYC-CDR3-YWGQGTRVTVSKK); the framework protein sequence pcNB2 is SEQ ID: 11—CDR1-SEQ ID NO:12—CDR2-SEQ ID NO:13—CDR3-SEQ ID NO:14 (i.e. MEVQLVEKGGGRVQAGGSLRLRCAAS-CDR1-WYRQAPGKQRELVAL-CDR2-ADSVKGRFRIRRD-NAKNTVYLRMRRLKPEDTAVYYC-CDR3-YWGQGTRVTVSK); the framework protein sequence pcNB3 is SEQ ID:15—CDR1-SEQ ID NO:16—CDR2-SEQ ID NO:17—CDR3-SEQ ID NO:18 (i.e., SEQ ID NO:9—MAQVQLVEKGGGKVRAGGKLRLRCTAS-CDR1-WFRQAPGQEREAVA-CDR2-RFKIKRDNAKNTVTL-RMNNLKPEDTAIYYCAA-CDR3-WGQGTRVTVSR); wherein CDR1, CDR2 and CDR3 are modified based on the target protein. In still another aspect, the polypeptide sequence comprises at least 80% identity to SEQ ID NO:7, SEQ ID NO:8, SEQ ID NO:9 and SEQ ID NO:10. In still another aspect, the modified framework region of the nanobody is a sequence comprising at least 80% identity to SEQ ID NO:11, SEQ ID NO:12, SEQ ID NO:13, and SEQ ID NO:14. In still another aspect, the modified framework region of the nanobody is a sequence comprising at least 80% identity to SEQ ID NO:15, SEQ ID NO:16, SEQ ID NO:17 and SEQ ID NO:18. For example, the modified framework region of the nanobody may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:7, 8, 9 and 10, or SEQ ID NO: 11, 12, 13 and 14, or SEQ ID NO: 15, 16, 17, and 18, provided the modified framework region maintains the polycationic surface.

Isolated polypeptides of the disclosure may be produced from nucleic acids molecules using molecular biological methods known to in the art. Generally speaking, a polynucleotide sequence encoding the polypeptide is inserted into a vector that is able to express the polypeptide when introduced into an appropriate host cell. Appropriate host cells include, but are not limited to, bacterial, yeast, insect, and mammalian cells. Once expressed, polypeptides may be obtained from cells using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the disclosure may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982).

Isolation of polypeptides is greatly aided when the polypeptide comprises a purification moiety.

iii. Vector

In another aspect, the present disclosure provides a vector comprising a nanobody construct of the disclosure. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

Specifically, the vector is an expression vector. The vector may have a high copy number, an intermediate copy number, or a low copy number. The copy number may be utilized to control the expression level for the nanobody construct, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

Expression vectors typically contain one or more of the following elements: promoters, terminators, ribosomal binding sites, and IRES. The term "promoter," as used herein, may mean a synthetic or naturally-derived molecule that is capable of conferring, activating, or enhancing expression of a nucleic acid. A promoter may comprise one or more specific transcriptional regulatory sequences to further enhance expression and/or to alter the spatial expression and/or temporal expression of a nucleic acid. A promoter may be constitutive, inducible/repressible or cell type specific. In certain embodiments, the promoter may be constitutive. Non-limiting examples of constitutive promoters include CMV, UBC, EF1α, SV40, PGK, CAG, CBA/CA-GGS/ACTB, CBh, MeCP2, U6 and H1. Non-limiting examples of inducible promoters include tetracycline, heat shock, steroid hormone, heavy metal, phorbol ester, adenovirus E1A element, interferon, and serum inducible promoters. Alternatively, the promoter may be cell type specific.

Expression of the nucleic acid molecules may be regulated by a second nucleic acid sequence so that the molecule is expressed in a host transformed with the recombinant DNA molecule. For example, expression of the nucleic acid molecules may be controlled by any promoter/enhancer element known in the art.

A nucleic acid encoding a nanobody construct may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

An expression vector encoding a nanobody construct may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding a nanobody construct that is introduced to the cell may be linear or circular, may be single-stranded or double-stranded, and may be DNA, RNA, or any modification or combination thereof.

An expression construct encoding a nanobody construct may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect. Upon introduction into the cell, an expression construct encoding a nanobody construct may be integrated into a chromosome. Integration of the expression construct encoding a nanobody construct into a cellular chromosome may be achieved with a mobile element.

Cells transfected with the expression construct encoding a nanobody construct generally will be grown under selection to isolate and expand cells in which the nucleic acid has integrated into a chromosome. Cells in which the expression construct encoding a nanobody construct has been chromosomally integrated may be maintained by continuous selection with the selectable marker. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

Nucleic acid molecules are inserted into a vector that is able to express the fusion polypeptides when introduced into an appropriate host cell. Appropriate host cells include, but are not limited to, bacterial, yeast, insect, and mammalian cells.

iv. Isolated Cell

In another aspect, the present disclosure provides an isolated cell comprising a vector of the disclosure. The cell may be a prokaryotic cell or a eukaryotic cell. Appropriate cells include, but are not limited to, bacterial, yeast, insect, and mammalian cells.

The isolated host cell comprising a vector of the disclosure may be used to produce a polypeptide encoded by a nanobody construct of the disclosure. Generally, production of a polypeptide involves transfecting isolated host cells with a vector comprising a nanobody construct and then culturing the cells so that they transcribe and translate the desired polypeptide. The isolated host cells may then be lysed to extract the expressed polypeptide for subsequent purification. "Isolated host cells" are cells which have been removed from an organism and/or are maintained in vitro in substantially pure cultures. A wide variety of cell types can be used as isolated host cells, including both prokaryotic and eukaryotic cells. Isolated cells include, without limitation, bacterial cells, fungal cells, yeast cells, insect cells, and mammalian cells.

In one embodiment, the isolated host cell is characterized in that after transformation with a vector of the disclosure, it produces the desired polypeptide for subsequent purification. Such a system may be used for protein expression and purification as is standard in the art. In some embodiments, the host cell is a prokaryotic cell. Non-limiting examples of suitable prokaryotic cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis*, *Enterobacter cloacae*, *Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive.

Particularly useful bacterial host cells for protein expression include Gram negative bacteria, such as *Escherichia coli*, *Pseudomonas fluorescens*, *Pseudomonas haloplanctis*, *Pseudomonas putida* AC10, *Pseudomonas pseudoflava*, *Bartonella henselae*, *Pseudomonas syringae*, *Caulobacter crescentus*, *Zymomonas mobilis*, *Rhizobium meliloti*, *Myxococcus xanthus* and Gram positive bacteria such as *Bacillus subtilis*, *Corynebacterium*, *Streptococcus cremoris*, *Streptococcus lividans*, and *Streptomyces lividans*. *E. coli* is one of the most widely used expression hosts. Accordingly, the techniques for overexpression in *E. coli* are well developed and readily available to one of skill in the art. Further, *Pseudomonas fluorescens*, is commonly used for high level production of recombinant proteins (i.e. for the development bio-therapeutics and vaccines).

Particularly useful fungal host cells for protein expression include *Aspergillis oryzae*, *Aspergillis niger*, *Trichoderma reesei*, *Aspergillus nidulans*, and *Fusarium graminearum*.

Particularly useful yeast host cells for protein expression include *Candida albicans*, *Candida maltose*, *Hansenula polymorpha*, *Kluyveromyces fragilis*, *Kluyveromyces lactis*, *Pichia guillerimondii*, *Pichia pastoris*, *Saccharomyces cerevisiae*, *Schizosaccharomyces pombe*, and *Yarrowia lipolytica*.

Particularly useful mammalian host cells for protein expression include Chinese hamster ovary (CHO) cells, HeLa cells, baby hamster kidney (BHK) cells, monkey kidney cells (COS), human hepatocellular carcinoma cells (e.g. Hep G2), human embryonic kidney cells, *Bos primigenius*, and *Mus musculus*. Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

II. Methods

In an aspect, the disclosure encompasses a method of preparing a cell-penetrating protein, comprising modifying a wild-type nanobody by mutating at least one amino acid residue in the framework region to arginine or lysine. A cell-penetrating protein is described in Section I, which is hereby incorporated by reference in its entirety.

In another aspect, a nanobody of the disclosure may be used in a method of binding a target protein. The method comprises providing a cell-penetrating nanobody, having binding affinity for the target protein and comprising a modified framework region having an exposed polycationic surface; and contacting the target protein with the cell-penetrating nanobody in the cytosol of a cell.

In still another aspect, a nanobody of the disclosure may be used in a method of detecting a target protein. The method comprises providing a cell-penetrating nanobody; and contacting the target protein with the cell-penetrating nanobody in the cytosol of a cell, wherein the cell-penetrating nanobody comprises a modified framework region having an exposed polycationic surface, has binding affinity for the target protein, and is fused to a reporter protein.

A target protein may be intracellular or extracellular to a target cell. A target protein may be on the surface of a target cell or inside a target cell. A target protein inside a target cell may be located in the cytosol of the cell. Specifically, a target protein may be an intracellular receptor within a target cell. The target cell may be in vitro, such as a commercially available cell line (e.g. American Type Culture Collection (ATCC)). The target cell may be derived from a mammalian cell. Alternatively, a target cell may be in vivo; i.e., the cell may be disposed in a subject. A subject may be a human or a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

A target cell may be any mammalian cell including, but not limited to a cancer cell, an immune system cell, and any other mammalian cell of interest. The cancer cell disposed may be disposed in a subject. The cancer cell may be a blood cancer cell (e.g., leukemia, lymphoma, myeloma) or a solid tumor cancer cell. Non-limiting examples of cancer cells include bladder cancer cells, bone cancer cells, brain cancer cells, breast cancer cells, central nervous system cancer cells, cervical cancer cells, colon cancer cells, colorectal cancer cells, duodenal cancer cells, endometrial cancer cells, esophageal cancer cells, eye cancer cells, gallbladder cancer cells, germ cell cancer cells, kidney cancer cells, larynx cancer cells, leukemia cells, liver cancer cells, lymphoma cells, lung cancer cells, melanoma cells, mouth/throat cancer cells, ovarian cancer cells, pancreatic cancer cells, prostate cancer cells, skin cancer cells, testicular cancer cells, thyroid cancer cells, vaginal cancer cells, and drug resistant cancer cells. Non-limiting examples of immune system cells include: phagocytes such as macrophages, neutrophils, and dendritic cells; mast cells; eosinophils; basophils; natural killer cells; B cells; and T cells such as killer T cells, helper T cells, and γδ T cells. The immune cells may further include immune cells at a particular activation state in various aspects.

A target protein is contacted with a cell-penetrating nanobody. A cell-penetrating nanobody is described in Section I, which is hereby incorporated by reference into this section in its entirety. If the target protein is disposed in a subject, the target protein is contacted with a cell-penetrating nanobody by administering the nanobody to the subject. The nanobody may be administered to the subject orally (as a solid or a liquid), parenterally (which includes intramuscular, intravenous, intradermal, intraperitoneal, and subcutaneous), or topically (which includes transmucosal and transdermal). An effective amount of the nanobody can be determined by a skilled practitioner in view of desired dosages and potential side effects of the nanobody.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

The frequency of dosing may be once, twice, three times or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Resurfaced Cell-Penetrating Nanobodies

Figure 1B:
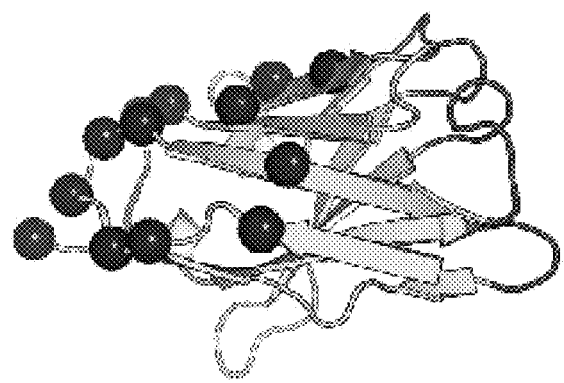
FIG. 1B depicts residues on NB1 that were mutated to either arginine or lysine to generate the resurfaced polycationic nanobody (pcNB1). Mutated residues are highlighted with spheres.

Studies began with a previously reported nanobody that binds Green Fluorescent Protein (GFP, FIG. 1A). Structural analysis of the nanobody that binds GFP (referred to as NB1, herein) revealed a large solvent-exposed surface consisting of a β-sheet and loop structure—called the framework region—that is distinct from the CDR loops. It was hypothesized that extensive polycationic resurfacing within this region by mutation of a critical number of residues to arginine (R) or lysine (K) (FIG. 1B, blue spheres) should endow cell penetration. The wild-type nanobody was mutated at 11 amino acid positions as described in FIG. 2A to create resurfaced polycationic GFP-binding nanobody (referred to as pcNB1, herein), which has a theoretical net charge of +14. Analogous polycationic resurfacing was performed on two other nanobodies, which bind HER2 or β-lactamase, respectively (referred to as NB2 or NB3, herein). The sequence of the wild-type nanobodies and resurfaced variants is shown in FIG. 2A. The resulting resurfaced polycationic nanobodies (referred to as pcNB2 or pcNB3, herein), have a theoretical net charge of +14 and +15, respectively. All three resurfaced polycationic GFP-binding nanobodies (pcNB1, pcNB2, and pcNB3) express in E. coli as soluble proteins (FIG. 2B).

The structural features of the wild-type and resurfaced nanobodies were assessed by circular dichroism. All nanobodies examined—wild-type and resurfaced variants—have a circular dichroism spectra similar to a previously reported nanobody (FIG. 2C). Collectively, expression of all resurfaced proteins in a soluble form, and similarities in the circular dichroism spectra of the wild-type and mutated variants, suggest that no dramatic structural changes occur as a result of polycationic resurfacing.

Example 2. Internalization of Resurfaced Nanobodies by Mammalian Cells

Figure 3A:
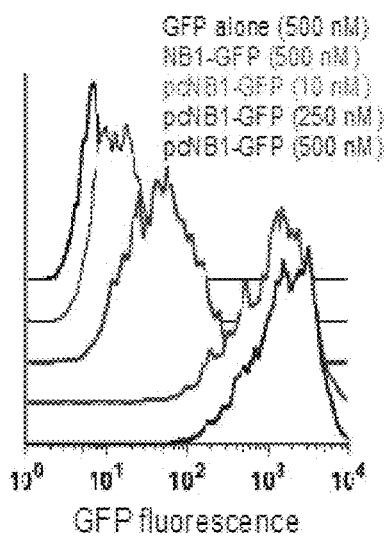
FIG. 3A, FIG. 3B, FIG. 3C depict flow cytometry data that supports concentration-dependent uptake of resurfaced polycationic nanobody-GFP fusion proteins, but not GFP alone (black line) or wild-type nanobody-GFP fusion (grey line). Red line=10 nM treatment; green line=250 nM treatment; blue line=500 nM treatment.
Figure 3B:
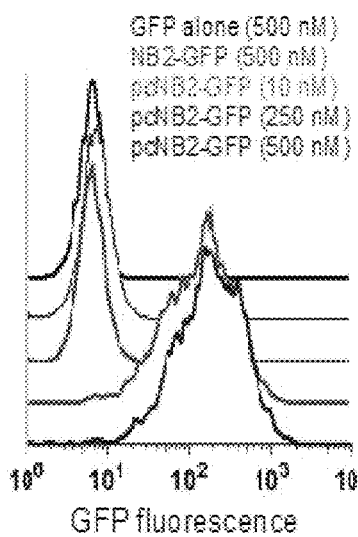
Figure 3C:
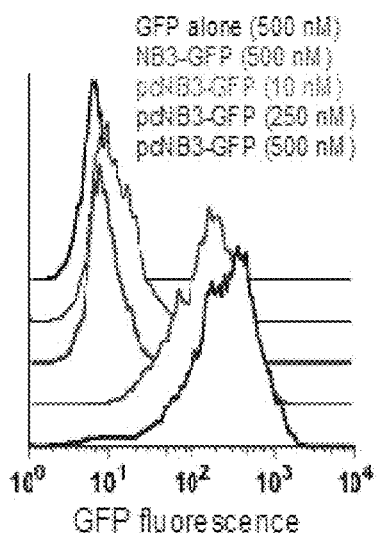
Figure 3D:
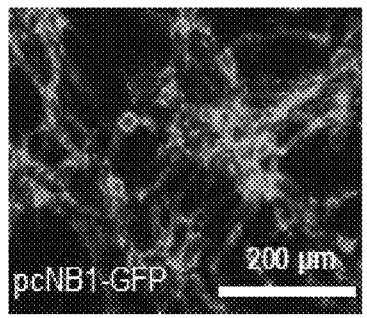
FIG. 3D, FIG. 3E, FIG. 3F depict fluorescence microscopy images of 3T3 cells following treatment with 250 nM resurfaced nanobody-GFP fusions.
Figure 3E:
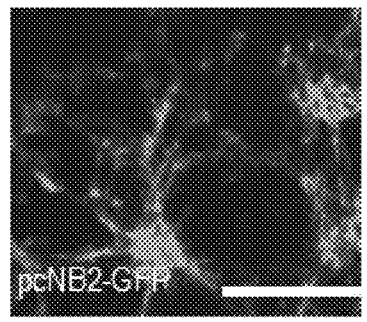
Figure 3F:
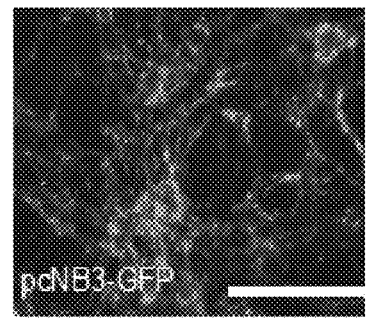

Polycationic resurfacing of a nanobody scaffold enables potent cell penetration, and the majority of the internalized nanobody accesses the cytosol. To determine uptake efficiency, resurfaced polycationic nanobodies were fused to GFP and measured uptake by flow cytometry. 3T3 cells were first treated with 10-500 nM resurfaced polycationic nanobody-GFP fusion, then washed with a phosphate buffered saline solution containing 20 U/mL heparin sulfate—which has been previously shown to remove cell surface bound protein especially supercharged proteins. Following treatment with trypsin, which also removes cell surface bound protein, intracellular nanobody-GFP was measured by flow cytometry. For each resurfaced nanobody, a concentration-dependent increase of internalized fusion protein was observed, as seen in FIG. 3A, FIG. 3B, FIG. 3C. In contrast, fusion proteins composed of the wild-type protein and GFP do not appreciably penetrate 3T3 cells (FIG. 3A, FIG. 3B, FIG. 3C). Internalization was further analyzed by fluorescence microscopy (FIG. 3D, FIG. 3E, FIG. 3F). Significant levels of each resurfaced nanobody-GFP fusion protein were observed in 3T3 cells, following the above described washing conditions to remove cell surface-bound protein.

Figure 3G:
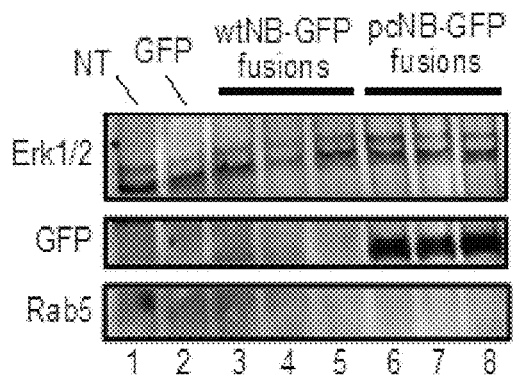
FIG. 3G depicts Western blot analysis of digitonin cell lysate for Erk1/2 (cytosolic marker), GFP (internalized resurfaced nanobody-GFP fusion protein), or Rab5 (endosome marker). Lane 1=no treatment; lane 2=wild-type GFP; lane 3=NB1-GFP fusion; lane 4=NB2-GFP fusion; lane 5=NB3-GFP fusion; lane 6=pcNB1-GFP fusion; lane 7=pcNB2-GFP fusion; lane 8=pcNB3-GFP fusion.
Figure 3H:
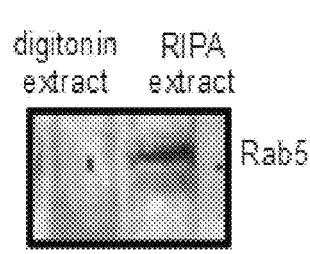
FIG. 3H depicts a Western blot showing no Rab5 (endosome marker) in cell lysate following digitonin lysis, but in extract following RIPA lysis.
Figure 5B:
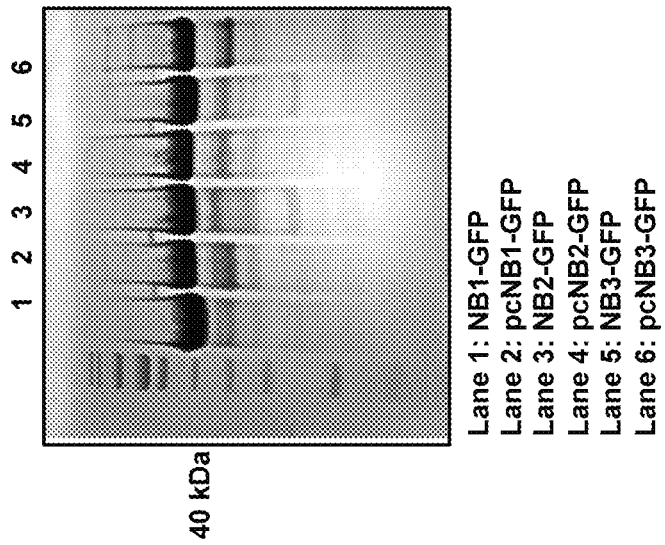
FIG. 5A and FIG. 5B depict SDS-PAGE analysis of purified WT nanobodies and polycationic resurfaced mutants without GFP (FIG. 5A) and with GFP (FIG. 5B).
Figure 5A:
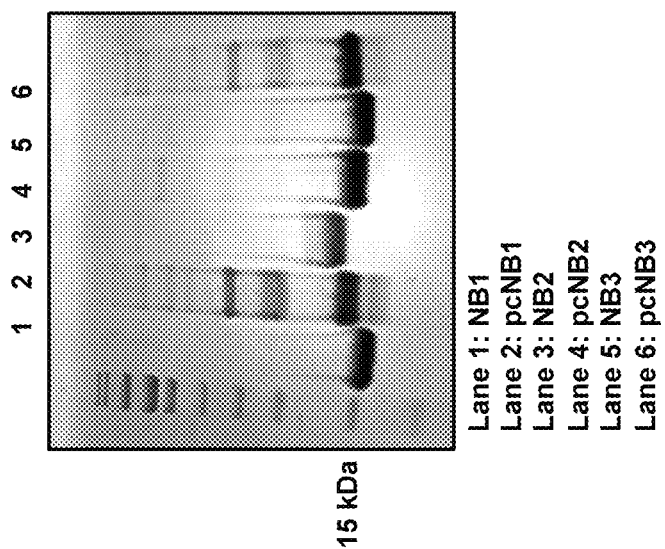
Figure 6A:
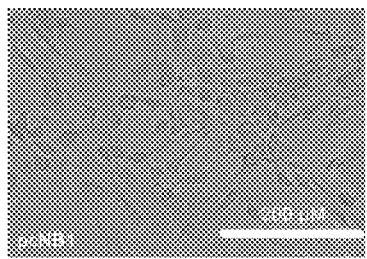
FIG. 6A, FIG. 6B and FIG. 6C depict brightfield images of 3T3 cells following treatment with 250 nM resurfaced nanobody-GFP fusions.
Figure 6B:
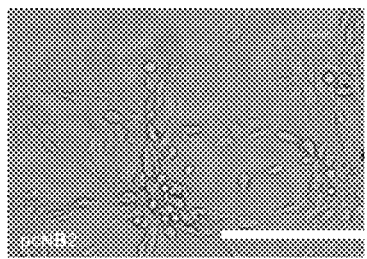
Figure 6C:
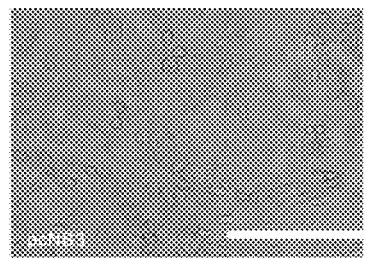
Figure 7A:
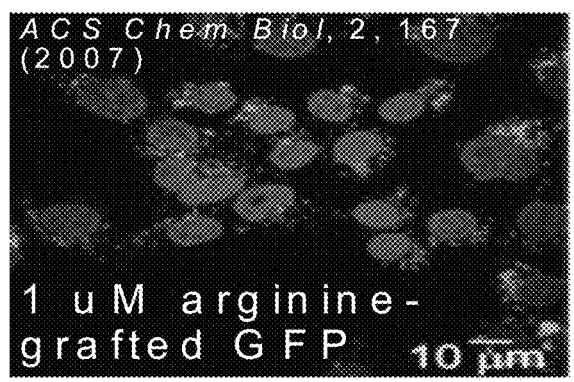
FIG. 7A and FIG. 7B depict fluorescent microscopy images for supercharged GFP variants with either 1 μM arginine-grafted GFP (FIG. 7A) or 50 nM supercharged GFP (FIG. 7B).
Figure 7B:
Figure 8B:
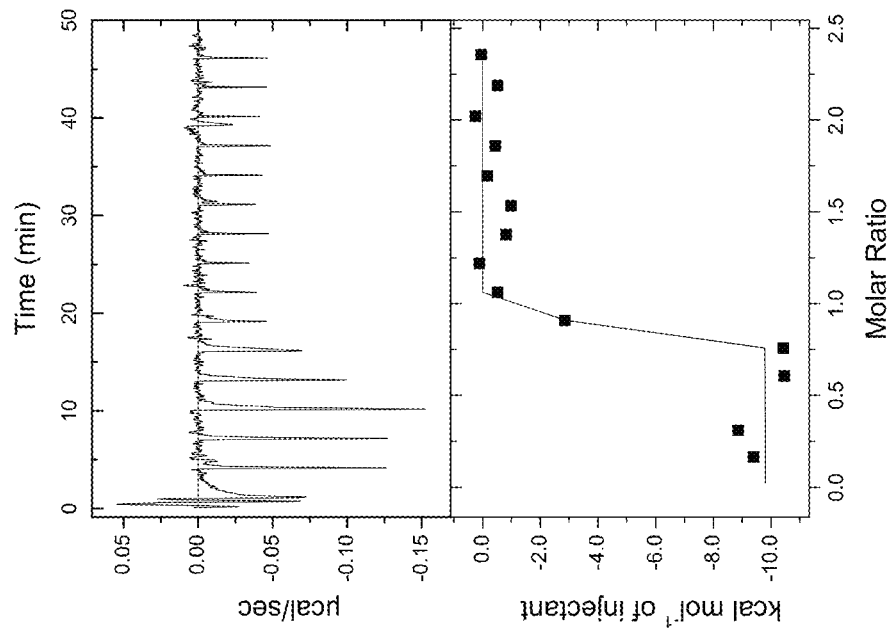
FIG. 8A and FIG. 8B depict representative ITC binding isotherms involving NB1 (FIG. 8A) and pcNB1 with EGFP (FIG. 8B).
Figure 8A:
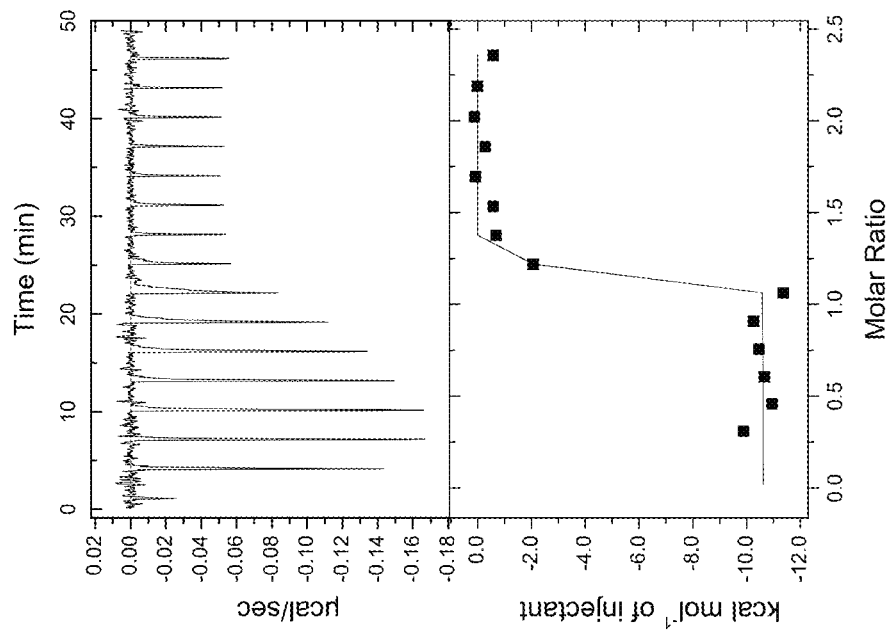

Interestingly, internalized arginine grafted GFP and supercharged GFP appear as punctate foci in fluorescence microscopy images—suggesting encapsulation within endosomes. However, the resurfaced nanobody-GFP fusions do not appear as such, suggesting that appreciable amounts of these internalized nanobodies might access the cytosol. This is critical, since the discovery of future cell-penetrating nanobodies based on these scaffolds would need to access the cytosol in order to engage therapeutically-relevant intracellular targets. This important aspect of cell uptake was further analyzed using a previously described method (Rabideau et al. *Chem Sci* 2015; 6: 648-653 and Liao et al. *Chem Bio Chem* 2014; 15: 2458, 2466, which are hereby incorporated by reference in their entirety). 3T3 cells were first treated with 250 nM nanobody-GFP or polycationic resurfaced nanobody-GFP fusions, then washed as described above to remove cell surface bound protein. Cells were then either lysed with a solution containing digitonin—which breaks the cell surface lipid bilayer, but not endosomes, or RIPA buffer, which breaks apart the lipid bilayers of the both the cell surface and endosomes. The cellular location of each internalized fusion protein (cytosolic or endosomal) was then assessed by Western blot, using an anti-GFP antibody (a marker for internalized fusion protein), anti-Erk 1/2 antibody (a marker for the cytosol) or anti-Rab5 antibody (a marker for endosomes). No appreciable amount of GFP or wild-type nanobody-GFP fusion is found within the cytosolic extraction (following cell lysis with digitonin, FIG. 3G, lanes 2-5), and no appreciable amount of Rab5 is observed (indicating that the lysis does not contain endosomes). In contrast, internalized resurfaced nanobody-GFP fusions appear in the cytosol—in the fraction that tests positive for the cytosolic marker Erk 1/2 but does not have any appreciable amount of the endosome marker Rab5 (FIG. 3G, lanes 6-8). Thus, the resurfaced polycationic protein is capable of dragging another protein (GFP) into the cytosol of a mammalian cell. In contrast to lysate obtained from treatment with digitonin, (Erk1/2 positive and Rab5 negative), lysis generated from RIPA buffer (which lyses the cell surface lipid bilayer and intracellular vesicles such as endosomes) tests positive for Rab5 (FIG. 3H). Thus, digitonin lysis does not contain endosomes. Collectively, these data indicate that GFP and wild-type nanobody-GFP fusions do not penetrate mammalian cells, which is supported by the flow cytometry data (FIG. 3A, FIG. 3B, FIG. 3C), but resurfaced polycationic nanobodies penetrate mammalian cells and high levels of the internalized protein accesses the cytosol.

Example 3. Retention of Resurfaced Nanobody Function

Having established that the resurfaced nanobodies penetrate mammalian cells and access the cytosol, it was next explored if this extensive mutagenesis alters function (compared to the wild-type nanobody). This is important, since the goal is to endow cell penetration, but maintain a structure capable of binding to a target (ultimately an intracellular target following CDR affinity maturation). Among the set of starting nanobodies, retention of function is most easily assessed using the GFP-binding nanobody, since its binding partner (GFP) is easily expressed and observed, and this interaction is particularly well characterized. In order to determine if polycationic resurfaced GFP-binding nanobody (pcNB1) still binds GFP in a living cell, $His_6$-labeled NB1 or pcNB1 and untagged GFP were co-expressed in *E. coli* from a pET-DUET plasmid. Following purification on nickel-NTA resin, purified proteins were analyzed by polyacrylamide gel electrophoresis (PAGE) and Coommassie staining. Unsurprisingly, untagged GFP co-purifies with $His_6$-NB1 (FIG. 4A, lane 2). Untagged GFP also co-purifies with the polycationic resurfaced variant $His_6$-pcNB1, suggesting that GFP affinity is retained, even in the chemically complex environment of a living cell (*E. coli*).

Example 4. Stability and Robustness of Resurfaced Nanobodies

It was next determined how polycationic resurfacing affects protein stability and robustness—important features when considering proteins as basic research tools and therapeutic leads. As previously stated, nanobodies are highly stable and robust proteins. Previous reports have shown that some nanobodies—including the GFP-binding nanobody—can be thermally denatured, but refold when cooled slowly. To see if the polycationic resurfaced GFP-binding nanobody (pcNB1) has the same level of stability and robustness, its ability to recover from thermal denaturation was tested. Both the wild-type $His_6$-labeled GFP-binding nanobody ($His_6$-NB1) and $His_6$-labeled polycationic resurfaced variant ($His_6$-pcNB1) were heated to 100° C. for 2 minutes, then allowed to cool to room temperature over the course of 2 hours. After cooling, the samples were incubated with cell lysate from *E. coli* that expresses recombinant GFP lacking a $His_6$ label. This solution was then incubated with nickel-NTA resin, the resin was washed, and nickel-bound protein was eluted with imidazole solution. Under these conditions, if $His_6$-NB1 and $His_6$-pcNB1 recover from thermal denaturation and regain function (GFP affinity), elution from the column should include both NB1 or pcNB1 and bound GFP. Eluted solutions were analyzed by a long wave (365 nm) hand-held lamp for the presence of GFP. No appreciable GFP fluorescence is seen when illuminating eluent from nickel-bound $His_6$-NB1 or $His_6$-pcNB1 (FIG. 4B, tubes 1-2). However, GFP fluorescence (indicating co-elution of the $His_6$-nanobody and bound GFP) is observed in eluent from nickel-bound $His_6$-NB1 and untagged GFP (FIG. 4B, tubes 3-4). Similar levels of GFP fluorescence is observed in eluent from nickel-bound $His_6$-pcNB1 and untagged GFP (FIG. 4B, tubes 5-6). As a positive control, eluent from nickel-bound $His_6$-GFP is similarly fluorescent (FIG. 4B, tube 7), and is contrasted by eluent from nickel-NTA treated with untagged GFP (FIG. 4B, tube 8). Collectively, these data show that untagged GFP does not have appreciable affinity for nickel-NTA, the nanobodies NB1 and pcNB1 are not appreciably fluorescent, and NB1 and pcNB1 are able to recover from thermal denaturation and bind GFP. Thus, polycationic resurfacing does not appreciably alter protein nanobody stability and robustness.

Discussion for the Examples

The inability of most proteins to penetrate mammalian cells greatly limits the identification of new protein therapeutics that bind and modulate disease-relevant intracellular targets. Proteins with engineered solvent-exposed cationic features penetrate mammalian cells, but a lack in general guidelines for such extensive mutagenesis, and the inability to perform such extensive mutagenesis on a number of therapeutically-relevant proteins, limits the broader application of this approach. In this disclosure, an alternative strategy has been provided. Specifically, a single protein scaffold has been disclosed that is amenable to polycationic resurfacing, is cell-penetrating, accesses the cytosol of mammalian cells, and can be evolved using in vitro or in vivo techniques to generate cell-penetrating proteins that bind and modulate intracellular disease-relevant targets.

As shown in the examples above, nanobodies can be resurfaced to display a polycationic feature. This mutagenesis results in a new nanobody that is potently cell-penetrating, but structure, function, and stability/robustness is maintained. Thus, polycationic resurfaced nanobodies can serve as a general scaffold for the discovery of protein basic research tools and therapeutic leads that target disease-relevant intracellular receptors.

Methods for the Examples

Cloning.

All plasmids were constructed on a pETDuet-1 backbone. All proteins were assembled from a set of overlapping oligonucleotides. Proteins were amplified using vent and the constructs were ligated into NcoI and NotI restriction enzyme cleavage sites in the pETDuet-1 plasmid. Proteins containing GFP fusions were assembled from a set of overlapping oligonucleotides and ligated into NcoI and KpnI restriction enzyme cleavage sites in the pETDuet-1 plasmid.

Protein Purification.

Plasmids were transformed into BL21s (DE3). Cells were grown in either 2500 or 500 mL LB cultures containing carbenicillin at 37° C. to $OD_{600}$=~0.6 and induced with 1 mM IPTG at 25° C. overnight. Cells were then collected by centrifugation and resuspended in either phosphate buffer with 150 mM NaCl for NBs (20 mM Sodium Phosphate, pH 7.4) or resuspended in phosphate buffer with 2 M NaCl for pcNBs (20 mM Sodium Phosphate, pH 7.4) and stored at −20° C. Frozen pellets were thawed and incubated with complete ULTRA protease inhibitors tablets then sonicated for 2 minutes. The lysate was cleared by centrifugation (9000 rpm, 20 minutes) and the supernatant was mixed with 1 mL Ni-NTA agarose resin for 30 minutes. The resin was collected by centrifugation (4950 rpm, 10 minutes). The resin was washed with 50 mL buffer and 20 mM imidazole then 10 mL buffer and 50 mM imidazole. The protein was then eluted with 7 mL buffer containing 300 mM imidazole. The proteins were dialyzed against buffer and analyzed for purity by SDS-PAGE. Purified proteins were quantified using absorbance at 280 nm.

Circular Dichosim.

Proteins were purified as described above. Separately, each protein was diluted to 6-8 uM in Sodium Phosphate buffer (20 mM Sodium Phosphate, pH 7.4 and 150 mM NaCl). Wavelength data are the average of three scans from 250 nm to 200 nm in 1 nm steps at 25° C.

Mammalian Cell Culture.

NIH/3T3 cells were cultured in Dulbecco's modified Eagle medium (DMEM) with 10% Fetal Bovine Serum (FBS). All cells were incubated at 37° C. with 5% $CO_2$ environment.

Live Cell Fluorescence Microscopy.

Mammalian cells were grown to ~80% confluency in a 6-well plate. Cells were then washed once with PBS and 2 mL of 250 nM protein fused with GFP was added. The cells were incubated with the protein solution for 3 hours at 37° C., 5% $CO_2$ environment. After the incubation period, cells were washed once with PBS and three times with PBS-HS (heparin sulfate 20 U/mL) for 10 minutes at 37° C., 5% $CO_2$. The cells were then imaged on the EVOS FL fluorescence microscope.

Flow Cytometry Analysis.

Mammalian cells were grown to 80% confluency in a 6-well plate. Cells were then washed once with PBS and 2 mL of 10 nM, 250 nM, or 500 nM protein fused with GFP was added. The cells were incubated with the protein solution for 3 hours at 37° C., 5% $CO_2$ environment. After the incubation period, cells were washed once with PBS and three times with PBS-HS (heparin sulfate 20 U/mL) for 10 minutes at 37° C., 5% $CO_2$. The cells were then removed from dish with 0.25% trypsin-EDTA and collected by centrifugation. The cells were then suspended in PBS and taken for flow cytometry analysis.

Cytosolic Protein Extraction and Whole Cell Lysate Preparation for Western Blot.

3T3 cells were plated in 6-well plate and grown to ~80% confluency. The cells were treated with 250 nM or 500 nM proteins (wtNB-GFP and pcNB-GFP or wtNB and pcNB, respectively) for 24 hours at 37° C., 5% $CO_2$. After treatment, cells were washed once with PBS and once with PBS-HS (heparin sulfate 20 U/mL) for 10 minutes at 37° C., 5% $CO_2$ then lifted with 0.25% trypsin-EDTA and pelleted. For cytosolic protein extraction, cell pellets were resuspended in 100 µL of 50 µg mL$^{-1}$ digitonin in 75 mM NaCl, 1 mM $NaH_2PO_4$, 8 mM $Na_2HPO_4$, 250 mM sucrose supplemented with Roche protease inhibitor cocktail for 10 minutes on ice. Cells were then centrifuged for 5 minutes at 13,000 rpm. Supernatant was then used as cytosolic protein extraction. Left over pellets were then resuspended in 100 µL RIPA buffer supplemented with Roche protease inhibitor cocktail and incubated on ice for 5 minutes then further lysed through a 20 gauge needle. Supernatant was then used as whole cell lysate extraction. Both supernatants were collected and separated by SDS-PAGE and transferred to a nitrocellulose membrane via an iBlot western blotting apparatus. The membrane was incubated in 1×TBS with 5% milk at 25° C. for 1 hour. The membrane was then washed 3 times with 1×TBS and 0.1% Tween-20. Primary antibodies for GFP, Erk1/2, and Rab5 were incubated with the membrane containing GFP fused nanobodies overnight in 10 mL of 1×TBS, 5% BSA, and 0.1% Tween-20 at 4° C. The western blot containing unfused nanobodies were incubated with primary antibodies for His6X, Erk1/2, and Rab5 overnight in same mixture. Both membranes were washed 3× with 1×TBS containing 0.1% Tween-20 and then incubated in Anti-Rabbit (Alexa Fluor 790) in 10 mL TBS, 5% milk and 0.1% Tween-20 for 1 hour at 25° C. The membrane was washed 3× with 1×TBS containing 0.1% Tween-20 and imaged in 1×TBS using the Odyssey Classic Infrared Imager.

Lysate Ni-NTA Pull-Down Assay.

wtNB1 and pcNB1 (nanobodies for GFP) tagged with $His_{6X}$ were cloned into MCS1 of pETDuet-1 using restriction enzymes NcoI and NotI. Untagged GFP was cloned into MCS2 of pETDuet-1 using restriction enzymes NdeI and KpnI. Completed constructs were transformed into BL21s (DE3). Cells containing the co-expressed pair were inoculated and induced as described previously. Cells were pelleted and purified as described previously. The pull-down was analyzed by SDS-PAGE.

What is claimed is:

1. A cell-penetrating nanobody comprising a modified framework region, wherein the modified framework region has one or more amino acid residues that are substituted as compared to a framework region of a wild-type nanobody and the modified framework region has an exposed polycationic surface.

2. The cell-penetrating nanobody of claim 1, wherein the one or more amino acid residues are substituted with arginine or lysine as compared to the framework region of the wild-type nanobody.

3. The cell-penetrating nanobody of claim 1, wherein the modified framework region has at least nine amino acid residues that are substituted with arginine or lysine as compared to the framework region of the wild-type nanobody.

4. The cell-penetrating nanobody of claim 1, having a theoretical net charge ranging from about +10 to about +35.

5. The cell-penetrating nanobody of claim 4, the theoretical net charge ranging from about +10 to about +20.

6. The cell-penetrating nanobody of claim 1, wherein the cell-penetrating nanobody is fused to a reporter protein.

7. The cell-penetrating nanobody of claim 6, wherein the reporter protein is chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune).

8. The cell-penetrating nanobody of claim 1, wherein the modified framework region comprises a framework protein sequence selected from the group consisting of pcNB1, pcNB2, and pcNB3.

9. The cell-penetrating nanobody of claim 1, wherein the framework region of the wild-type nanobody comprises a framework protein sequence selected from the group consisting of NB1, NB2, and NB3.

10. A method of preparing a cell-penetrating protein having a modified framework region, comprising modifying a wild-type nanobody by mutating at least one amino acid residue in the framework region of the wild-type nanobody to arginine or lysine such that the modified framework region has an exposed polycationic surface.

11. The method of claim 10, comprising modifying the wild-type nanobody by mutating at least nine amino acid residues in the framework region to arginine or lysine.

12. The method of claim 10, wherein the cell-penetrating protein has a theoretical net charge ranging from about +10 to about +35.

13. The method of claim 12, wherein the theoretical net charge ranges from about +10 to about +20.

14. The method of claim 10, wherein the nanobody is fused to a reporter protein.

15. The method of claim 14, wherein the reporter protein is chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune).

16. The method of claim 10, wherein the wild-type nanobody is modified by mutating amino acid residues in the framework region to arginine or lysine so that the framework region comprises a framework protein sequence selected from the group consisting of pcNB1, pcNB2, and pcNB3.

17. The method of claim 10, wherein the framework region of the wild-type nanobody comprises a framework protein sequence selected from the group consisting of NB1, NB2, and NB3.

* * * * *

SEQUENCE LISTING

```
<160> NUMBER OF SEQ ID NOS: 18

<210> SEQ ID NO 1
<211> LENGTH: 123
<212> TYPE: PRT
<213> ORGANISM: Camelidae sp.

<400> SEQUENCE: 1

Met Gln Val Gln Leu Val Glu Ser Gly Gly Ala Leu Val Gln Pro Gly
1               5                   10                  15
```

Gly Ser Leu Arg Leu Ser Cys Ala Ala Ser Gly Phe Pro Val Asn Arg
            20                  25                  30

Tyr Ser Met Arg Trp Tyr Arg Gln Ala Pro Gly Lys Glu Arg Glu Trp
            35                  40                  45

Val Ala Gly Met Ser Ser Ala Gly Asp Arg Ser Tyr Glu Asp Ser
 50                  55                  60

Val Lys Gly Arg Phe Thr Ile Ser Arg Asp Asp Ala Arg Asn Thr Val
 65                  70                  75                  80

Tyr Leu Gln Met Asn Ser Leu Lys Pro Glu Asp Thr Ala Val Tyr Tyr
                85                  90                  95

Cys Asn Val Asx Val Gly Phe Glu Tyr Trp Gly Gln Gly Thr Gln Val
                100                 105                 110

Thr Val Ser Ser Lys His His His His His His
            115                 120

<210> SEQ ID NO 2
<211> LENGTH: 125
<212> TYPE: PRT
<213> ORGANISM: Camelus dromedarius

<400> SEQUENCE: 2

Met Glu Val Gln Leu Val Glu Ser Gly Gly Gly Leu Val Gln Ala Gly
 1               5                   10                  15

Gly Ser Leu Arg Leu Ser Cys Ala Ala Ser Gly Ile Thr Phe Ser Ile
            20                  25                  30

Asn Thr Met Gly Trp Tyr Arg Gln Ala Pro Gly Lys Gln Arg Glu Leu
            35                  40                  45

Val Ala Leu Ile Ser Ser Ile Gly Asp Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Lys Arg Phe Arg Thr Ala Ala Gln Gly Thr Asp Tyr Trp Gly Gln Gly
                100                 105                 110

Thr Gln Val Thr Val Ser Ser His His His His His His
            115                 120                 125

<210> SEQ ID NO 3
<211> LENGTH: 136
<212> TYPE: PRT
<213> ORGANISM: Camelus dromedarius

<400> SEQUENCE: 3

Met Ala Gln Val Gln Leu Val Glu Ser Gly Gly Gly Ser Val Gln Ala
 1               5                   10                  15

Gly Gly Ser Leu Arg Leu Ser Cys Thr Ala Ser Gly Gly Ser Glu Tyr
            20                  25                  30

Ser Tyr Ser Thr Phe Ser Leu Gly Trp Phe Arg Gln Ala Pro Gly Gln
            35                  40                  45

Glu Arg Glu Ala Val Ala Ala Ile Ala Ser Met Gly Gly Leu Thr Tyr
 50                  55                  60

Tyr Ala Asp Ser Val Lys Gly Arg Phe Thr Ile Ser Arg Asp Asn Ala
 65                  70                  75                  80

Lys Asn Thr Val Thr Leu Gln Met Asn Asn Leu Lys Pro Glu Asp Thr
                85                  90                  95

```
Ala Ile Tyr Tyr Cys Ala Ala Val Arg Gly Tyr Phe Met Arg Leu Pro
            100                 105                 110

Ser Ser His Asn Phe Arg Tyr Trp Gly Gln Gly Thr Gln Val Thr Val
        115                 120                 125

Ser Ser His His His His His His
        130                 135

<210> SEQ ID NO 4
<211> LENGTH: 123
<212> TYPE: PRT
<213> ORGANISM: Artificial Sequence
<220> FEATURE:
<223> OTHER INFORMATION: SYNTHESIZED

<400> SEQUENCE: 4

Met Gln Val Gln Leu Val Glu Lys Gly Gly Lys Arg Val Gln Pro Gly
1               5                   10                  15

Gly Ser Leu Arg Leu Lys Cys Ala Ala Ser Gly Phe Pro Val Asn Arg
            20                  25                  30

Tyr Ser Met Arg Trp Tyr Arg Gln Ala Pro Gly Lys Glu Arg Glu Trp
        35                  40                  45

Val Ala Gly Met Ser Ser Ala Gly Asp Arg Ser Ser Tyr Glu Asp Ser
    50                  55                  60

Val Lys Gly Arg Phe Lys Ile Lys Arg Asp Asp Ala Arg Asn Thr Val
65                  70                  75                  80

Tyr Leu Arg Met Arg Lys Leu Lys Pro Glu Asp Thr Ala Val Tyr Tyr
                85                  90                  95

Cys Asn Val Asn Val Gly Phe Glu Tyr Trp Gly Gln Gly Thr Arg Val
            100                 105                 110

Thr Val Ser Lys Lys His His His His His
        115                 120

<210> SEQ ID NO 5
<211> LENGTH: 125
<212> TYPE: PRT
<213> ORGANISM: Artificial Sequence
<220> FEATURE:
<223> OTHER INFORMATION: SYNTHESIZED

<400> SEQUENCE: 5

Met Glu Val Gln Leu Val Glu Lys Gly Gly Arg Val Gln Ala Gly
1               5                   10                  15

Gly Ser Leu Arg Leu Arg Cys Ala Ala Ser Gly Ile Thr Phe Ser Ile
            20                  25                  30

Asn Thr Met Gly Trp Tyr Arg Gln Ala Pro Gly Lys Gln Arg Glu Leu
        35                  40                  45

Val Ala Leu Ile Ser Ser Ile Gly Asp Thr Tyr Tyr Ala Asp Ser Val
    50                  55                  60

Lys Gly Arg Phe Arg Ile Arg Arg Asp Asn Ala Lys Asn Thr Val Tyr
65                  70                  75                  80

Leu Arg Met Arg Arg Leu Lys Pro Glu Asp Thr Ala Val Tyr Tyr Cys
                85                  90                  95

Lys Arg Phe Arg Thr Ala Ala Gln Gly Thr Asp Tyr Trp Gly Gln Gly
            100                 105                 110

Thr Arg Val Thr Val Ser Lys His His His His His
        115                 120                 125
```

```
<210> SEQ ID NO 6
<211> LENGTH: 136
<212> TYPE: PRT
<213> ORGANISM: Artificial Sequence
<220> FEATURE:
<223> OTHER INFORMATION: SYNTHESIZED

<400> SEQUENCE: 6

Met Ala Gln Val Gln Leu Val Glu Lys Gly Gly Lys Val Arg Ala
1               5                   10                  15

Gly Gly Lys Leu Arg Leu Arg Cys Thr Ala Ser Gly Ser Glu Tyr
                20                  25                  30

Ser Tyr Ser Thr Phe Ser Leu Gly Trp Phe Arg Gln Ala Pro Gly Gln
            35                  40                  45

Glu Arg Glu Ala Val Ala Ala Ile Ala Ser Met Gly Leu Thr Tyr
    50                  55                  60

Tyr Ala Asp Ser Val Lys Gly Arg Phe Lys Ile Lys Arg Asp Asn Ala
65                  70                  75                  80

Lys Asn Thr Val Thr Leu Arg Met Asn Asn Leu Lys Pro Glu Asp Thr
                85                  90                  95

Ala Ile Tyr Tyr Cys Ala Ala Val Arg Gly Tyr Phe Met Arg Leu Pro
            100                 105                 110

Ser Ser His Asn Phe Arg Tyr Trp Gly Gln Gly Thr Arg Val Thr Val
        115                 120                 125

Ser Arg His His His His His His
    130                 135

<210> SEQ ID NO 7
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 7

Met Gln Val Gln Leu Val Glu Lys Gly Gly Lys Arg Val Gln Pro Gly
1               5                   10                  15

Gly Ser Leu Arg Leu Lys Cys Ala Ala Ser
                20                  25

<210> SEQ ID NO 8
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 8

Met Arg Trp Tyr Arg Gln Ala Pro Gly Lys Glu Arg Glu Trp Val Ala
1               5                   10                  15

Gly

<210> SEQ ID NO 9
<211> LENGTH: 37
<212> TYPE: PRT
<213> ORGANISM: Artificial Sequence
<220> FEATURE:
<223> OTHER INFORMATION: SYNTHESIZED

<400> SEQUENCE: 9

Tyr Glu Asp Ser Val Lys Gly Arg Phe Lys Ile Lys Arg Asp Asp Ala
1               5                   10                  15
```

Arg Asn Thr Val Tyr Leu Arg Met Arg Lys Leu Lys Pro Glu Asp Thr
            20                  25                  30

Ala Val Tyr Tyr Cys
        35

<210> SEQ ID NO 10
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 10

Tyr Trp Gly Gln Gly Thr Arg Val Thr Val Ser Lys Lys
1               5                   10

<210> SEQ ID NO 11
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 11

Met Glu Val Gln Leu Val Glu Lys Gly Gly Arg Val Gln Ala Gly
1               5                   10                  15

Gly Ser Leu Arg Leu Arg Cys Ala Ala Ser
            20                  25

<210> SEQ ID NO 12
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 12

Trp Tyr Arg Gln Ala Pro Gly Lys Gln Arg Glu Leu Val Ala Leu
1               5                   10                  15

<210> SEQ ID NO 13
<211> LENGTH: 36
<212> TYPE: PRT
<213> ORGANISM: Artificial Sequence
<220> FEATURE:
<223> OTHER INFORMATION: SYNTHESIZED

<400> SEQUENCE: 13

Ala Asp Ser Val Lys Gly Arg Phe Arg Ile Arg Arg Asp Asn Ala Lys
1               5                   10                  15

Asn Thr Val Tyr Leu Arg Met Arg Leu Lys Pro Glu Asp Thr Ala
            20                  25                  30

Val Tyr Tyr Cys
        35

<210> SEQ ID NO 14
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 14

Tyr Trp Gly Gln Gly Thr Arg Val Thr Val Ser Lys

```
<210> SEQ ID NO 15
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 15

Met Ala Gln Val Gln Leu Val Glu Lys Gly Gly Lys Val Arg Ala
1               5                   10                  15

Gly Gly Lys Leu Arg Leu Arg Cys Thr Ala Ser
            20                  25

<210> SEQ ID NO 16
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 16

Trp Phe Arg Gln Ala Pro Gly Gln Glu Arg Glu Ala Val Ala
1               5                   10

<210> SEQ ID NO 17
<211> LENGTH: 32
<212> TYPE: PRT
<213> ORGANISM: Artificial Sequence
<220> FEATURE:
<223> OTHER INFORMATION: SYNTHESIZED

<400> SEQUENCE: 17

Arg Phe Lys Ile Lys Arg Asp Asn Ala Lys Asn Thr Val Thr Leu Arg
1               5                   10                  15

Met Asn Asn Leu Lys Pro Glu Asp Thr Ala Ile Tyr Tyr Cys Ala Ala
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 18

Trp Gly Gln Gly Thr Arg Val Thr Val Ser Arg
1               5                   10
```